United States Patent [19]

Moake

[11] Patent Number: 5,012,091

[45] Date of Patent: Apr. 30, 1991

[54] PRODUCTION LOGGING TOOL FOR MEASURING FLUID DENSITIES

[75] Inventor: Gordon L. Moake, Houston, Tex.

[73] Assignee: Halliburton Logging Services, Inc., Houston, Tex.

[21] Appl. No.: 485,703

[22] Filed: Feb. 27, 1990

[51] Int. Cl.[5] ............................................. G01V 5/12
[52] U.S. Cl. .................................. 250/266; 250/262; 250/265; 250/269
[58] Field of Search ............... 250/269, 264, 265, 266, 250/262

[56] References Cited

U.S. PATENT DOCUMENTS

| | | | |
|---|---|---|---|
| 4,492,865 | 1/1985 | Murphy et al. | 250/254 |
| 4,558,220 | 12/1985 | Evans | 250/266 |
| 4,737,636 | 4/1988 | Smith, Jr. | 250/269 |
| 4,864,129 | 9/1989 | Paske et al. | 250/269 |
| 4,939,362 | 7/1990 | Supernaw et al. | 250/269 |

Primary Examiner—Carolyn E. Fields
Assistant Examiner—Drew A. Dunn
Attorney, Agent, or Firm—William J. Beard

[57] ABSTRACT

A fluid density measuring tool is set forth, a structure having a shielded sonde supporting a radiation source having a characteristic gamma ray emission pattern preferably in all directions of azimuth, and a cooperative first detector is disclosed. Ports aligned with the first detector and source preferably limit the gamma ray pathway primarily to the fluid surrounding the tool. Additional detectors are included, and they measure gamma radiation which involves a surrounding casing and other materials about the well. This provides sufficient measurement data enabling one to sort the data and thereby determine the bulk density of the fluid in the well.

18 Claims, 1 Drawing Sheet

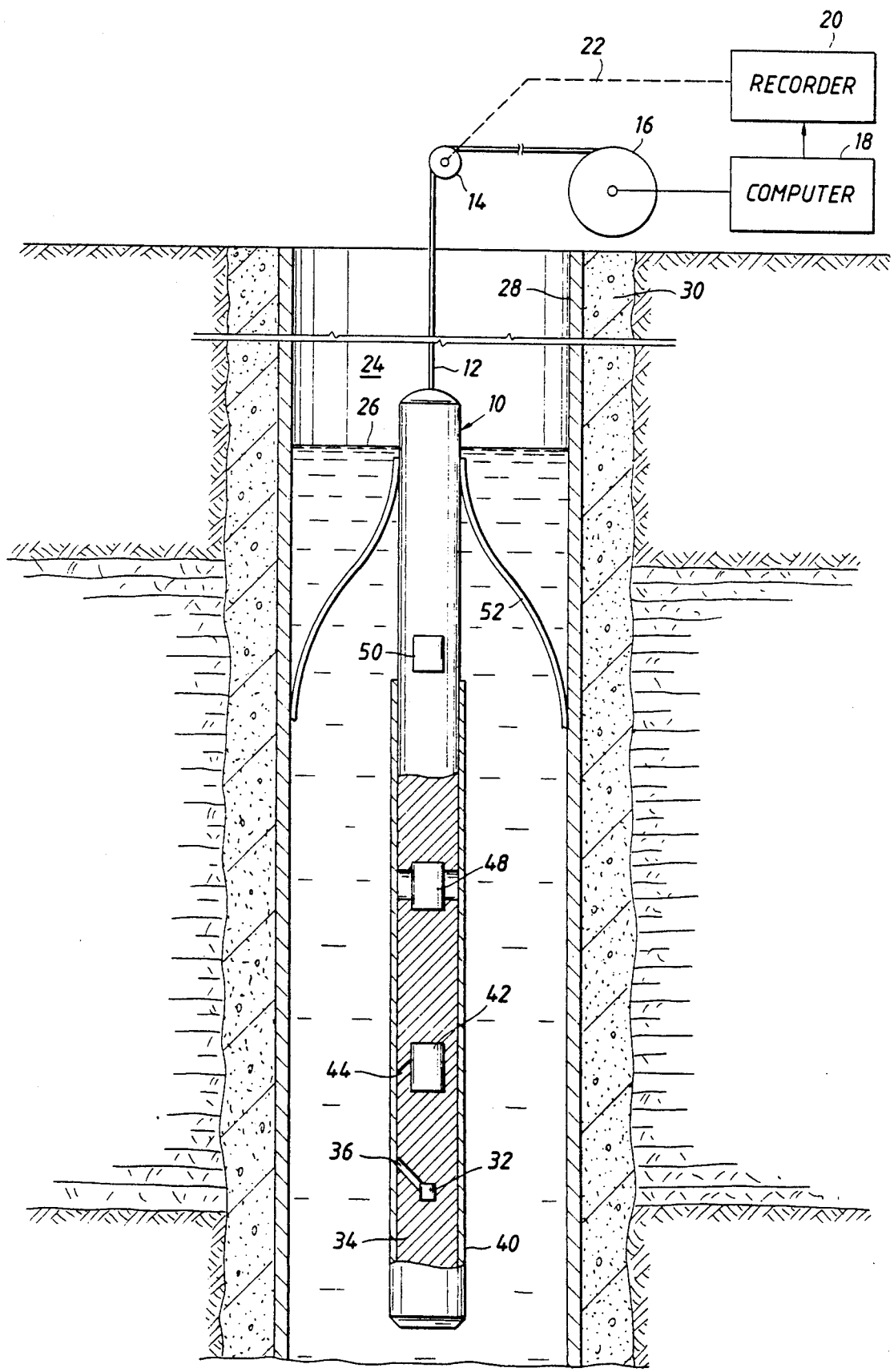

PRODUCTION LOGGING TOOL FOR MEASURING FLUID DENSITIES

BACKGROUND OF THE DISCLOSURE

A production logging tool which measures the density of the production fluid in a well borehole, particular a cased well, typically funnels the fluid into the tool where density measurements are made. Many tools operate by measuring the attenuation of gamma rays emanating from a radioactive source which directs the radiation through the fluid to a detector. One disadvantage of this approach is that the well fluid is disturbed during measurement, yielding a density value that is not indicative of the fluid in the well bore. Moreover, such a measurement is only an average measurement and cannot measure asymmetries in the density distribution as a function of radial direction. The column of fluid in a well may stratify if it has been standing for any interval or is slowly flowing. Water will settle to the bottom and the oil will rise to the top. This is a problem in a slant hole, or, a highly deviated well, where the density differential between oil, water and gas can cause the fluid to stratify, with the oil and gas rising to the high side of the hole. The present disclosure is directed to a device which will measure fluid density and provide a measurement of density in all radial directions, and which will also indicate density variations along the length of the tool. The present disclosure sets out a radioactive radiation source which is a typical radioactive isotope, typically one with a long half life. One approach is to provide shielding which is so located that impinging gamma rays reaching the detector pass only through the fluid around the tool. The detector is surrounded by shielding arranged in this fashion. Accordingly, the gamma rays which impinge on the detector travel only through the fluid. When the gamma rays emitted by the source are scattered by the fluid, those deflected to the detector will provide a fairly direct measure. As a generalization, the signal is proportionate to electron density of the materials along the path of travel of the gamma rays impinging on the detector. Generally, gamma radiation through the fluid interacts with the fluid by Compton scattering. While other types of scattering are possible, the great probability is that the scattering is Compton scattering only. Since Compton scattering depends on the density of electrons in the medium, which is related to the bulk density, the extent of scattering depends on the bulk density of the medium, or the fluid which surrounds the tool. In the event, however, that the gamma rays emitted by the source enter the pipe (primarily steel) or enter the adjacent or surrounding cement and formations, there are other interactions between the gamma rays and the materials which make up the steel pipe concrete and adjacent formations. At this juncture, there will be a statistically measurable scattering of gamma rays by coherent scattering or photoelectric absorption.

If the tool is centralized, it is axiomatic that a gamma ray which passes through the well pipe must first pass through the fluid. Generally, if all of the gamma rays must traverse the fluid and very few of the gamma rays that do enter the pipe are ultimately detected, then the materials making up the pipe and surrounding structure are less important to the scattering mechanism. In that instance, the fluid density can be determined from the count rate of a single detector. So to speak, a single measurement yields a single unknown or variable referring to the electron density of the fluid and hence, the bulk density of the fluid. By contrast, if a significant number of the gamma rays that enter the pipe are scattered back to the detector, then the measured count rate to some extent depends on the absorptive properties of the pipe and the materials which are on the exterior of the pipe. In that instance, a single measurement cannot be used to provide two variables, one relating to the bulk density of the well fluid and the other relating to the bulk density of the pipe and materials beyond the pipe. In that instance, a single count rate simply will not provide sufficient data to determine two variables from one measurement. It is, however, possible to have two detectors which make two separate measurements and the two measurements can be used to determine two variables, namely, one from the fluid electron density or the bulk density of the fluid. The other measurement relates to the pipe and other confining materials beyond the pipe. A further factor in making measurements is preferably the incorporation of shielding and collimators which are axially symmetric so that resultant measurements provide an average of the fluid density fully around the tool. In other words, the radiation is transmitted from the source in all directions of azimuth. By this approach, all of the fluid which is in the borehole can be tested and data thereby obtained representative of all of the fluid.

Alternately, it is possible to collimate the source and detector so that the preferred range of illumination by the radiation source is limited to a specified azimuthal range, e.g., irradiation at an azimuth of thirty degrees width. In that instance, the tool can be used where the port is directed along a particular azimuth line, data taken at that angle, and then the tool can be rotated to other angular directions. This is particularly helpful in deviated holes where the fluid composition can vary significantly with angle. Of course, it is advantageous to use a navigational package to correlate the angular measurements to an absolute direction.

The foregoing mentions a single detector system and then a two detector system where two detectors in effect provide measurements yielding two variables. By the use of a third detector, another variable can be obtained. Because the detectors will be placed at different distances from the source, on average the gamma rays detected by a detector will have traveled farther from the tool in a radial direction than gamma rays detected by a detector closer to the source. Thus, the count rate of the detector closest to the source will be most sensitive to the fluid closest to the tool, whereas the middle detector will be more sensitive to the fluid farther from the tool. The detector farthest from the source will be most sensitive to the casing and cement. Thus, information from the three detectors can be used to determine the fluid density near the tool and the fluid density farther from the tool.

The present disclosure also contemplates the use of a detector which is capable of determining count rates in particular energy windows. For instance, in the use of a scintillator with a photomultiplier tube (hereinafter PMT), the energy spectra from the detector can be classified into specific energy windows. In general terms, the low energy gamma rays will have traveled further through the fluid than high energy gamma rays. Accordingly, the sensitivity to the surrounding media at different distances from the tool will vary with the energy window. thus, one detector could measure two count rates, one that is primarily sensitive to the fluid density, and one that has a greater sensitivity to the casing. The two count rates could be combined to provide a measure of the fluid density that is independent of the casing. Also, the different energy windows could be used with two or more detectors. The fluid density could then be determined independently for the different energy windows, yielding densities that correspond to different distances from the tool.

In general, the measurement will be improved if the tool is centralized in the hole. The centralization can be implemented with a passive device that clamps on to the tool or with a powered centralizer.

In summary, the present apparatus is a fluid density measuring system utilizing a source and preferably two or three detectors. Shielding material can be incorporated to collimate the irradiation from the source, and the detectors can likewise be collimated to receive gamma ray radiation from specific directions. Moreover, the ports or windows which emit the radiation from the source or direct radiation toward the detectors can either be 360° or include lesser angles. In any event, a determination of fluid density can be derived, and to the extent that the fluid density is determined, it can be determined free of factors relating to the surrounding steel casing and other materials.

BRIEF DESCRIPTION OF THE DRAWINGS

So that the manner in which the above recited features, advantages and objects of the present invention are attained and can be understood in detail, more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

The only drawing shows a fluid density measuring device utilizing a source and multiple detectors wherein the device is incorporated in the sonde lowered on a logging cable in a well borehole.

DETAILED DESCRIPTION OF THE PREFERRED EMBODIMENT

Attention is directed to the only drawing which illustrates a sonde 10 supported in a well on a logging cable 12 which encloses one or more electrical conductors for delivery of signals to the surface. The logging cable 12 passes over a sheave 14, and is spooled or stored on a reel or drum 16. The electrical conductors are connected by suitable conductors to a CPU 18 which carries out certain calculations and presents data as will be described. The data is provided to a recorder 20 and is recorded when the sonde at a particular depth. The sonde depth is indicated by an electrical or mechanical depth measuring system 22 which is operated by movement of the sheave 14 so that depth measurements are provided to the recorder 20.

The well 24 has fluid 26 in it which can be flowing or not dependent on the rate of production of the well. The purpose of the present invention is to describe a fluid density measuring system. The fluid in the well can readily extend to the surface of the well. The well is ordinarily lined with a casing which is made of steel, primarily ferrous, carbon and trace elements. The casing 28 is held in position by cement which is cured to form a surrounding concrete layer 30. That surrounds the steel casing and holds it in position to prevent leakage along the exterior of the well.

The sonde includes and encloses various data processing equipment which is believed to be well known. There are certain radiation responsive detectors which form outputs which are in the form of pulses. These pulses are typically converted by an analog to digital converter into digital form and are transmitted to the surface in a particular data transfer format. Moreover, there is a telemetry system and suitable line drivers for connection with the cable 12.

A source 32 is located in the sonde. It is surrounded by shielding material 34. The shielding collimates the gamma rays emitted by the source. They are emitted through a fully encircling window 36 which is directed in all directions of azimuth and upwardly at an angle. The shielding material is typically tungsten or lead. It is in the form of an elongate cylindrical structure which is enclosed within a skin or housing 40 around the tool. The housing is generally transparent to the emitted gamma rays. The window or port 36 preferably fully encircles the tool in one embodiment. More will be noted about alternate embodiments later. The shielding material encompasses or encloses a detector 42. The detector is provided with a window or port 44 directed radially through the shielding material. As will be seen, the preferred path for the radiation is through the window or port 36, into the fluid, and scattering into the port 44 for detection. The detector 42 is thus exposed to gamma radiation deriving from the source 32. The shielding material extends upwardly along the tool and encloses another detector 48. The detector 48 is provided with a larger exposure circumferentially fully thereabout. So to speak, the port 48 is wide so that gamma radiation can impinge over a relatively wide window. As drawn, the shielding material appears to be segmented in the drawing. It is, however, held in position by the shell 40 which defines the structure of the detector system 10. The upper portions of the sonde above the shielding preferably include the appropriate electronic system necessary for transmission of the data to the surface. A flexible centralizer 52 is attached to keep the tool centered in the borehole.

The count rate at the detector 42 is related to the density of the fluid. Speaking very generally, this can be given by the simple equation $C_{42} = F(\rho)$. In this instance, $\rho$ is the electron density of the fluid and in this instance, that is proportional to the fluid density. In other words, this measurement can relate count rate to fluid density, and with a suitable constant for calibration purposes, the fluid density can be given by the count rate $C_{42}$.

The foregoing statement is true primarily if the path of the gamma radiation is from the port 36 into the fluid and into the port 44. If that statement holds true, then the count measurement is related to one variable, namely fluid density, and the value of density can be quickly obtained. Another possibility exists, however, namely that the gamma radiation may be directed into or even through the steel casing 28, perhaps into the concrete 30 or even farther into the adjacent formations. If that is the situation, then a different relationship prevails, namely where the count rate $C_{42}$ is given by $F(\rho, \rho_0)$. In this relationship, the density $\rho_0$ is a composite resulting from the steel pipe and other materials beyond the steel pipe. Assuming that this is the relationship, it is impossible to convert the data obtained thereby so that one measurement provides two variables. If, however, $\rho_0$ is sufficiently small that it can be ignored, then the equation given earlier can be used so that a single variable provides a single measurement.

The detector 48 provides a second measurement. Generally, the count rate of the detector 48 provides a relationship where $C_{48}$ equals $F_1(\rho,\rho_0)$. This is a different function and a different relationship in contrast with that for the count rate $C_{42}$. Looking at both equations, it is generalized that measurements $C_{42}$ and $C_{48}$, if both used, will provide two variables which can be solved to determine, from two equations, the two unknowns which are $\rho$ and $\rho_0$. As a generalization, these relationships are, in fact, different so that two equations with two unknowns are provided and are amenable to solution.

The tool may also include a third detector 50. In this case, the fluid can be conceptually divided into two regions, one near the tool and one further from it, and these two regions can be assigned densities $\rho_1$ and $\rho_2$. Using $\rho_0$ to represent the effective density of the casing, the count rates from the three detectors can be represented by three different functions, $F(\rho_1, \rho_2, \rho_0)$, $F_1(\rho_1, \rho_2, \rho_0)$, and $F_2(\rho_1, \rho_2, \rho_0)$. Since there are three measurements and three unknowns, the count rates can be used to determine $\rho_1$ and $\rho_2$.

The foregoing relationships are true where the irradiation is uniform in all directions of azimuth. It is possible, however, to close off a portion of the port 36, for instance, to leave a window which is only thirty degrees in width. Preferably, the port 44 for the detector 42 is made similarly narrow. The same can be done for the other detectors. If that is done, the device becomes directional in azimuth. This is desirable because, from time to time, the tool can be rotated to provide different readings in different directions. This is important in operation because the simplified representation of the fluid 26 may not prevail in slant holes. For instance, the tool can be located in a slant well at a forty-five degree angle with respect to the vertical, and the fluid may stratify with hydrocarbons collected on the top and water on the bottom. In that instance, irregular reading would be obtained as a function of azimuth with respect to the axis of the logging tool.

In an alternate embodiment, only one detector 42 consisting of a scintillation type detector and a photomultiplier tube is used. The detector provides information on the energy of the detected gamma rays. Count rates are then developed, using standard techniques, that correspond to different energy windows. In the simplest form, only two energy windows are used, which yields two count rates corresponding to high-energy and low-energy gamma rays, $C_l$ and $C_h$. These count rates are related to the density of the fluid and casing through two different functions, $F(\rho,\rho_0)$ and $F_1(\rho, \rho_0)$. Thus, the two count rates can be used to solve for $\rho$.

The foregoing sets forth the preferred embodiment but the scope thereof is determined by the claims which follow.

What is claimed is:

1. A method of determining the density of fluids in a well borehole susceptible of difference in fluid density along the well borehole comprising the steps of:

(a) positioning a sonde supported radiation source in a well borehole;

(b) positioning a first sonde supported radiation detector in the well borehole and similar but more remotely spaced second and third radiation detectors in the well borehole;

(c) emitting radiation from the source to interact with electrons of fluids in the well borehole wherein the radiation interacts with the fluid of the well borehole;

(d) measuring the count rate at the first, second, and third detectors as a result of emitting radiation from the source to thereby obtain first, second, and third count rates from the three respective detectors; and (e) from the three measured count rates, determining the fluid density of fluid which is closer to the first detector and separately the density of fluid which is nearer the third detector wherein the determinations are substantially independent of response to the materials at the sidewall of the well borehole as a result of radiation impingement thereof.

2. The method of claim 1 including the step of shaping shielding around the radiation source and the first detector to thereby direct radiation primarily through fluid in the well borehole, and in a direction reducing the likelihood of interaction between the radiation and electrons of the materials forming the sidewall of the well borehole.

3. The method of claim 1 wherein the radiation is emitted in 360° of azimuth with respect to the sonde.

4. The method of claim 1 including the step of shielding the source and/or first detector to control the direction of radiation impingement.

5. The method of claim 1 wherein the sonde is centralized in the well borehole.

6. The method of claim 1 including the step of positioning a sonde at a specified well depth in fluid in the well borehole and measuring the depth of the sonde.

7. The method of claim 1 including the step of shielding the first detector to limit the direction of radiation impingement.

8. The method of claim 7 including the step of shielding the second detector to limit the direction of radiation impingement.

9. The method of claim 1 including the step of shielding the radiation source to limit the direction of radiation emission therefrom.

10. The method of claim 1 including the step of emitting radiation in all directions of azimuth about the radiation source.

11. The method of claim 1 including the step of emitting radiation over a limited angle of azimuth from the radiation source.

12. The method of claim 1 including the step of shielding the first spaced detector to limit the direction of impingement of radiation resulting from interaction of the radiation source with the materials beyond the radiation source.

13. The method of claim 12 including the step of shielding the second detector to limit the direction of radiation impingement.

14. The method of claim 1 including the step of positioning the third spaced detector which is spaced farther than the second spaced detector from the radiation source and measuring radiation impinging thereon as a result of interaction of emitted radiation from the source with materials beyond the source, and measuring the count rate at the third detector; from the count rates in the three detectors, determining the density of the fluid closest to the tool and the density of the fluid farthest from the tool, substantially independent of response to the materials at the sidewall of the well bore.

15. The method of claim 14 wherein the sonde is centralized in the well borehole.

16. The method of claim 14 including the step of positioning a sonde at a specified well depth in fluid in the well borehole and measuring the depth of the sonde.

17. The method of claim 14 wherein one detector of two or more detectors provides energy information and is used to measure count rates from two or more energy windows, and the count rates are then combined to determine fluid densities corresponding to different radial regions around the sonde.

18. The method of claim 14 wherein the radiation is emitted in 360° of azimuth with respect to the sonde.

* * * * *